United States Patent [19]

Cotte et al.

[11] 4,293,543

[45] Oct. 6, 1981

[54] PROCESS AND COMPOSITION FOR THE COLORATION OF KERATIN-CONTAINING SUBSTANCES

[75] Inventors: Jean-Marie Cotte, Saint-Cyr-Au-Mont; Philippe Potin, Billere, both of France

[73] Assignee: Societe Nationale Elf Aquitaine, Courbevoie, France

[21] Appl. No.: 193,397

[22] Filed: Oct. 2, 1980

[30] Foreign Application Priority Data

Oct. 3, 1979 [FR] France ............................. 79 24627
Sep. 26, 1980 [FR] France ............................. 80 20720

[51] Int. Cl.$^2$ .................. A61K 7/42; A61K 7/12; A61K 7/13
[52] U.S. Cl. ............................. 424/59; 8/404; 8/405; 8/526; 8/587; 222/94; 8/436
[58] Field of Search .............. 424/59; 8/404, 405, 8/406, 407, 435, 436, 526, 527, 587, 607, 608; 222/94

[56] References Cited

U.S. PATENT DOCUMENTS 3,931,912  1/1976  Hsiung .................................. 8/405
4,173,453  11/1979  Shiah .................................. 8/405

*Primary Examiner*—Donald B. Moyer
*Attorney, Agent, or Firm*—Ostrolenk, Faber, Gerb & Soffen

[57] ABSTRACT

A process and composition for coloring substances and tissues containing keratin, by means of an agent or co-reactant having a ketone or aldehyde function. An amino-acid, in particular a thio-amino-acid, is contacted with the substance to be colored. The composition can be in the form of a solution or a suspension containing the amino-acid, applicable separately from or together with the co-reactant of known type based on a ketone or aldehyde. The invention is useful in cosmetics, for tanning the skin or coloring the hair or nails. It is also applicable to the coloration of various articles, in particular hair in general, feathers, horn, shell etc.

14 Claims, 1 Drawing Figure

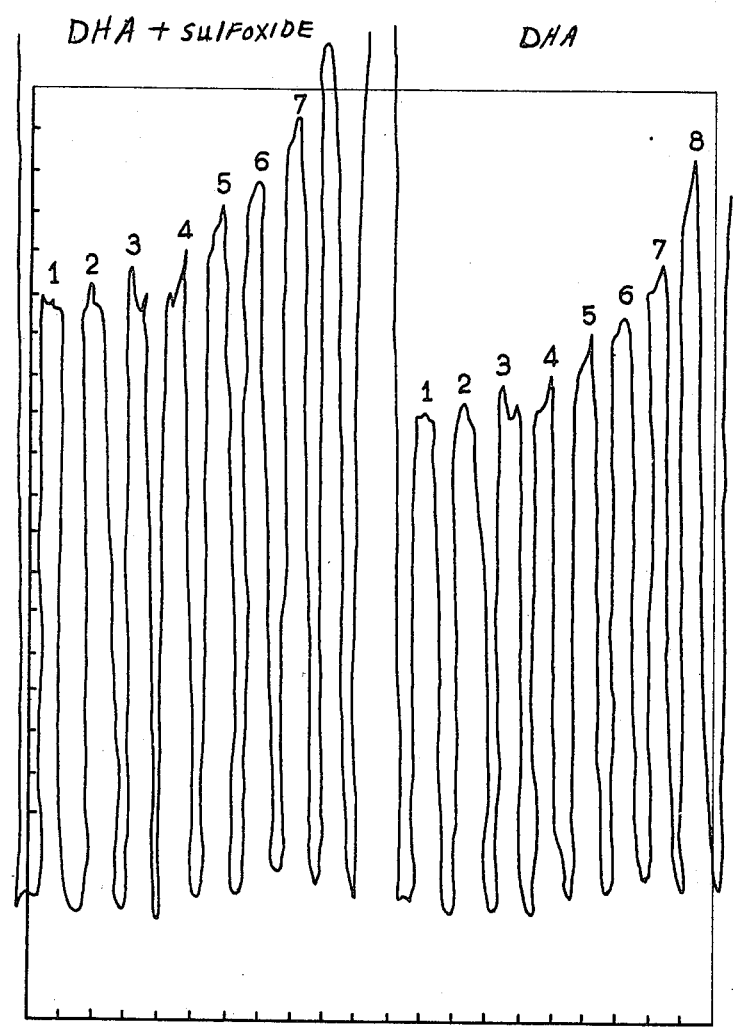

PROCESS AND COMPOSITION FOR THE COLORATION OF KERATIN-CONTAINING SUBSTANCES

DESCRIPTION

The invention relates to a process and a composition for the colouration of keratin-containing substances, particularly tissues such as skin and substances such as hair (both on the head and other hair), nails, feathers, hooves, horns, etc. It provides an improvement in the colouration of such materials.

Products for development of the colouration of the human skin, currently called bronzing or tanning, by the reaction of these products with the natural amino-acids constituting human tissue, are well known in the art. Also, a certain amount of work has been carried out regarding the utilization of non-injurious products which permit the development upon the skin of a colouration of natural appearance. The products employed most at the present time include compounds having a ketone or aldehyde function, often also containing an alcohol function. Thus, in various bronizing compositions, substances are used such as dihydroacetone, glyceraldehyde, erythrulose, alloxane, tartaric aldehyde, aldehydo-dimethoxysuccinic or benzylamino-hydroxysuccinic aldehyde. These various substances give a brown colouration by combination with the amino-acids present in the sebum or in the first horny layer of the epidermis by a known mechanism, namely the Maillard reaction. However, the distribution and nature of the amino-acids in the organism are not uniform on the surface of the skin. The intensity and shade of the colour obtained vary considerably from one place to another on the treated skin. Moreover, the colourations obtained according to the known art do not resist washing well and fade quite rapidly with time. Another disadvantage is the often the duration required for development of the colour is too long, during which time the active substance can become eliminated by simple immersion in water or by sweating. Clothing impregnated with sebum can also become stained.

The present invention provides an improvement which allows the above-mentioned disadvantages to be avoided. It makes it possible to obtain a uniform colouration over all the surface treated, which resists washing better and develops more rapidly than is the case with known compositions. Moreover, the process and the composition according to the invention can be employed not only upon human skin, but also upon various human and animal tissues. The invention is thus utilizable in furriery, in the treatment of feathers and also for the nails and hair, e.g. in hairdressing.

The present invention results from the unexpected discovery that the colouration of keratinic substances or tissues by compounds having ketone or aldehyde functions can be intensified by applying a sulphoxide-amino-acid to the substance or the tissue treated. This can be done just before treatment with the colouring agent itself, slightly after the treatment or simultaneously with it. Improvement in the appearance and duration of the colouration, indicated above, are then found.

The process according to the invention comprises treating the keratin-containing substance or tissue with a solution of an amino-acid before, during or after application of an aldehydic or ketonic compound, the colouring agent also being called a coreactant.

Sulphoxy-amino-acids utilizable according to the invention can be selected from compounds of the type:

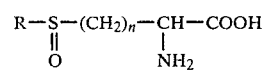

where R is an organic group which can have one or more S, O and/or N atoms connected to carbon atoms, which preferably are $C_1$ to $C_6$, and n is an integer from 1 to 4. Particularly favouravle results are obtained with methionine-sulphoxide:

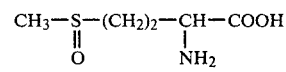

and with the mono- and di-sulphoxides of cystine:

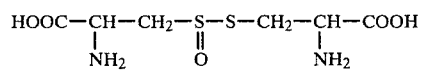

or

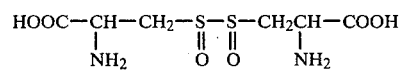

Sulphoxy-amino-acids, among others, have the advantage in comparison with the corresponding thioamino-acids of a greater solubility in water, which allows more concentrated solutions to be obtained. Methionine-sulphoxide, for example, is more than six times more soluble than methionine. Also, this sulphoxide is non-toxic, like methionine itself. The presence of the sulphoxide function permits penetration and fixation in the corneal layer of the amino-acid and the coloured complex derived from it. Moreover, preparations made from this amino-acid are free from odour.

The composition for carrying out the process according to the invention is constituted by a combination of two solutions or dispersions, one of which contains the standard colouration agent or coreactant, while the second contains one or more amino-acids dissolved in water. The solution or dispersion of the colouration agent itself can comprise various customary adjuvants, such as fatty acids, higher alcohols, surface-active agents and so on, the nature and proportions of which vary with the nature of the tissue or the substance to be treated, in other words, whether concerning colouration of the skin, hair, feathers, horn etc., the adjuvants for the colouration co-reactant being selected according to the known technique which thus need not be described here.

As regards the amino-acid, it can be formulated alone in the form of a solution or emulsion, particularly as a milk or cream, but it can also be usefully accompanied by surface-active agents, softening agents, UV filter agents, compositions facilitating penetration into organic tissues and so on.

The two solutions or dispersions are intended to be mixed at the time of use or also to be applied successively, one after the other, to the material to be treated. While the proportions of the products to be employed can vary considerably, for instance, 1 to 10 moles of the ketonic or aldehydic co-reactant for 1 to 10 moles of the sulphoxy-amino-acid, a preferred feature of the invention is to use 1 mole of the ketonic or aldehydic co-reactant per 1 mole of amino-acid.

According to a particular embodiment of the invention, an aqueous solution can be employed containing both the ketonic or aldehydic co-reactant and the sulphoxy-amino-acid, provided the pH of this solution is adjusted to a value not exceeding 4, for example 2 to 4 and, preferably, 3 to 3.9. This results from the discovery that ketonic and aldehydic solutions of this kind are not stable at pH values above 4 and that solutions of the sulphoxy-amino-acids change above pH 5 by releasing an odour. On the other hand, the co-reactants do not react with sulphoxy-amino-acids when the pH is in the acid range. The optimum pH for the reaction is 7 to 8.

The preferred embodiment of the invention consists in utilizing two solutions stored separately: I-a mixture of the co-reactant and the sulphoxy-amino-acid in water at a pH not exceeding 4 and, II-a basic solution to be mixed with solution I at the time of use, the resultant solution having a pH of at least 7 and preferably from 7 to 8.

As already indicated above, the invention can be carried out with various ketones and aldehydes containing hydroxyl or —NH groups, in particular 1,3-dihydroxypropanone-2, $HOCH_2-\underset{\underset{O}{\|}}{C}-CH_2OH$, 1,3,4-tri-hydroxybutanone-2 (erythrulose), $HOCH_2-CHOH-\underset{\underset{O}{\|}}{C}-CH_2OH$, 2,3-dihydroxypropanal-1 (glyceraldehyde), $HOCH_2-CHOH-\underset{\underset{O}{\|}}{CH}$, alloxane

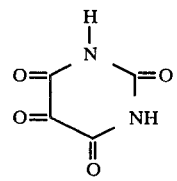

2,3-dihydroxydibutanal-1,4 (tartaric aldehyde),

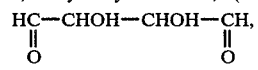

and other substances having an aldehyde or ketone function known to have "bronzing" or tanning properties on the skin.

The invention is illustrated by the non-limitative examples which follow.

EXAMPLE 1

An aqueous solution I was prepared, containing 0.72 mole of methionine per liter at a pH adjusted to 3.5 by the addition of hydrochloric acid. 1.6 moles per liter of dihyroxyacetone (DHA) was dissolved in this solution.

On the other hand, a solution II of 0.5 mole of monopotassium phosphate with 0.41 mole of NaOH per liter was prepared. Solution I remained stable while not neutralized. At the time of use, solutions I and II were mixed so as to obtain a mixture having a pH of 7.45. This mixture contained 2.22 moles of ketone per mole of amino-acid. The mixture was maintained at 33° C. and development of colour was monitored by measuring the optical density after times ranging from 24 to 96 hours. As the coloured complex does not present its maximum in the visible range, the measurements were effected under very near ultraviolet radiation, at 420 nm, on the above mixture diluted by 1/10.

The table below gives the optical densities found for the various mixtures. These were the averages of 3 or 4 measurements. In the column of measurements made after 3 hours, the optical densities given were measured on the non-diluted mixture, while the other colunms relate to liquids diluted by 1/10. M designates the mixture in which the amino-acid is methionine. S corresponds to the mixture where the amino-acid is methionine-sulphoxide and AA designates the mixture of 16 amino-acids present in the conjunctive layer of the dermis, that is to say a mixture of amino-acids in which serine and citrulline predominate (composition determined by Spier and Pascher).

|   | Pure | Diluted by 1/10 | | | |
|---|---|---|---|---|---|
|   | 3h | 24h | 48h | 72h | 96h |
| M | 0.035 | 0.14 | 0.24 | 0.34 | 0.30 |
| S | 0.067 | 0.21 | 0.39 | 0.47 | 0.48 |
| AA | 0.065 | 0.16 | 0.27 | 0.37 | 0.37 |

It can be seen that methionine-sulphoxide (line S) added to DHA produced a colouration of the mixture more rapidly than obtained with natural amino-acids (AA) and led to a much higher final intensity; optical density of 0.47 after 72 hours instead of 0.37.

EXAMPLE 2

Tests by application to the skin of volunteer subjects were carried out with the following two creams, the compositions of which are indicated by weight:

| | Cream 1 | |
|---|---|---|
| I | Monodipalmito stearate of polyoxyethylene glycol ("Tefose 1500") | 6 |
| | Stearic acid | 1 |
| | Cetyl alcohol | 2 |
| | Oleic polyoxyethylene glycerides | 5 |
| | Isopropyl myristate | 5 |
| | | 19 |
| II | Stabilizer: parahydroxybenzoic ester | 0.15 |
| | Methionine-sulphoxide | 4.3 |
| | Water | 65.5 |
| | HCl in a quantity sufficient for pH = 3.5 | |
| | | 69.95 |

The aqueous solution II was introduced into the fatty dispersion I with moderate agitation after both had been warmed to 70° C. To the final cooled cream, 1.5 part of DHA was then added.

| | Cream 2 | | |
|---|---|---|---|
| I | Stearic acid 19 + Water | 55 | |
| II | Potash tablets | 2 | (for pH = 9); water 13 |
| | Sodium hydroxide tablets | 0.8 | |
| III | Glycerol | 10 | |

The basic solution II was progressively introduced into the suspension I, maintained at 70° C. with moderate agitation, and then the glycerol III was added. The mixture, cooled to ambient temperature, had a pH of 9. By spreading an equivalent volume of each of these creams 1 and 2 on the skin, a mixture was obtained which had a pH of 7 to 8. This test was carried out on the skin of 10 volunteer patients at the rate of 7.5 mg per cm$^2$. On control zones, only cream 3 was applied, which contained the agent developing the colouration.

Results of these tests are summarized in the Table below.

| Cream 3 | | |
|---|---|---|
| I | Monodipalmitostearate of polyethylene glycol | 8 |
| | Cetyl alcohol | 1 |
| | Vaseline oil | 6 |
| | Lanoline | 2 |
| | | 17 |
| II | Glycerol | 3.2 |
| | Stabilizer: parahydroxybenzoic ester | 0.15 |
| | Water | 6.3 |
| | | 9.65 |

The two mixtures I and II were heated to 70° C., after which the solution II was poured into the fatty dispersion I with moderate agitation. 0.56 part by weight of the colouring agent, DHA, was introduced into the mixture so obtained.

It will be noted that with 10 patients the ketone alone gave an average colouration after 3 hours, whereas application of cream 1 containing methionine-sulphoxide gave after 3 hours a very strong colouration with 2 patients, a strong one with 6 and an average one with 2. Measurements after 2 and 5 days showed an improved resistance to washing of the zones which had received methionine-sulphoxide.

EXAMPLE 3

Two zones of 9 squares 2×2 cm were prepared on the thigh. One served as a control and received cream 3, namely DHA alone as in Example 2, the other was the test zone and received cream 1 containing methionine-sulphoxide and the basic cream 2. One square of each zone was treated every hour for 9 hours with 30 mg of the cream and the test area was photographed 9 hours after the first application.

Operative conditions for photography:
Diapositive film 160 ASA (artificial light);
Illumination with 4 lamps each of 250 W situated approximately 50 cm from the surface to be photographed;
CANON FTP camera mounted on a tripod and situated 60 cm from the subject;
Shutter speed: 1/250;
Diaphragm 6.6.

The surface of the skin was covered with a white gauze shield which only allowed the treated zones to appear.

Measurements:

The intensity of the colouration of each square was measured by measuring the optical density of the diapositives with the aid of a photodensitometer. The accompanying FIGURE shows the more rapid development of the colouration and the stronger intensity obtained with application of the cream containing methionine-sulphoxide.

EXAMPLE 4

Two subjects free from browning, one blonde and the other brown, were both treated with cream 1 of Example 2 containing DHA and methionine-sulphoxide and then with the alkaline cream 2. After 3 hours, the colouration had attained its maximum in the two cases and presented an excellent uniformity of intensity and shade, with the exception of some rarely-exposed particular corneal zones, such as the elbows, the knees and the heels.

EXAMPLE 5

A subject having vitiligo was treated on the depigmentation zones with cream 1 containing methionine-sulphoxide and then with the basic cream 2.

After 3 hours, a tint similar to that of the peripheral zones developed, attenuating the unfavourable effect of the condition.

EXAMPLE 6

A lock of hair of a pale blonde shade was immersed in a 5% aqueous solution of methionine-sulphoxide and then in a 2% aqueous solution of DHA, pH 7. After 5 hours, a dark brown tint developed. It resisted shampooing.

EXAMPLE 7

The cream 2 of Example 2 was replaced with the following cream:

I Stearic acid 20+triethanolamine 0.5+water 41
II Potassium hydroxide tablets 0.77+caustic soda tablets 0.27+water 21
III Sorbitol 6+glycerol 3.5+water Q.S. 100

The phases I, II and III were mixed in that order and under the same conditions used for the preparation of the cream of Example 2. The mixture of the two creams, spread on the skin in substantially equal volumes, had a pH in the range from 7 to 8.

TABLE

| Subject | Time of appearance of colour | |
|---|---|---|
| | Zone I | Zone II |
| 1 | 1h | ½h |
| 2 | 1h 30 | 1h |
| 3 | 2h | 1h 30 |
| 4 | " | " |
| 5 | " | 1h |
| 6 | " | " |
| 7 | " | " |
| 8 | " | " |
| 9 | 3h | 3h |
| 10 | " | " |

| | Intensity after 3 hours | | Intensity after 48 hours | | Intensity after 5 days, with washing each day | |
|---|---|---|---|---|---|---|
| | Zone I | Zone II | Zone I | Zone II | Zone I | Zone II |
| 1 | ++ | ++++ | ++ | ++++ | + | +++ |
| 2 | ++ | ++++ | ++ | ++++ | + | +++ |
| 3 | ++ | +++ | ++ | +++ | + | ++ |
| 4 | ++ | +++ | ++ | +++ | + | ++ |
| 5 | ++ | +++ | ++ | +++ | + | ++ |
| 6 | ++ | +++ | ++ | +++ | + | ++ |
| 7 | ++ | +++ | ++ | +++ | + | ++ |
| 8 | ++ | +++ | ++ | +++ | + | ++ |
| 9 | ++ | ++ | 0 | 0 | 0 | 0 |
| 10 | ++ | ++ | 0 | 0 | 0 | 0 |

Zone I: 2% DHA Cream alone
Zone II: 5% sulphoxide + 5% DHA Cream
++++: very strong colouration
+++: strong colouration
++: average colouration
+: weak colouration 0: zero colouration

We claim:

1. A process for the colouration of a keratin-containing substance or tissue by means of a colouration agent having a ketone or aldehyde function favouring the development of colouration in the substance or tissue, in which an amino-acid is applied to the latter before, during or after treatment with the colouration agent, wherein the amino-acid contains a sulphoxy group.

2. A process according to claim 1, in which the sulphoxy-amino-acid is methionine-sulphoxide.

3. A process according to claim 1 in which the sulphoxy-amino-acid is the mono- or di-sulphoxide of cystine.

4. A process according to any one of claims 1 to 3, in which the proportions of the colouration agent and the amino-acid are such that they occur on the substance or tissue to be treated in the ratio 1 to 10 moles of the agent per 1 to 10 moles of the amino-acid, the pH of the resulting mixture being 7 to 8.

5. A process according to claim 4 in which the proportion is one mole of coloring agent per mole of sulphoxy-amino acid.

6. A process according to claim 1 in which the keratin containing substance or tissue is skin, hair, nails, fur, feathers, horns or shells.

7. A composition for use in carrying out the process of claim 1 characterized in that it comprises an aqueous solution or dispersion of a ketonic or aldehydic coloring agent and a sulphoxy-amino acid having a pH below 4.

8. A composition according to claim 7 containing 1 to 10 moles of the ketonic or aldehydic compound per 1 to 10 moles of the ketonic or aldehydic compound per 1 to 10 moles of amino acid and having a pH of 3-3.9.

9. A composition according to claim 8 having one mole of ketonic or aldehydic compound per mole of amino acid.

10. A composition according to claim 8 or 9 in which the amino acid is selected from the group consisting of methionine sulphoxide, cystine monosulphoxide and cystine disulphoxide.

11. A package for carrying out the process according to claim 1, characterized in that it comprises two aqueous solutions or dispersions, the first of which contains the ketonic or aldehydic colouration agent and a sulphoxy-amino-acid and has a ph below 4, and the second of which is a basic medium, the proportions of the two solutions or dispersions being such that their mixture has a pH of 7 to 8.

12. A package according to claim 11, characterized in that the amino-acid is methionine-sulphoxide.

13. A package according to claim 11 or 12, characterized in that it contains 1 to 10 moles of a ketonic or aldehydic compound capable of colouring the skin per 1 to 10 moles of amino acid.

14. A package according to claim 13 characterized in that it contains one mole of ketonic or aldehydic compound per mole of sulphoxy-amino acid.

* * * * *